United States Patent [19]

Herbert et al.

[11] Patent Number: 4,762,275

[45] Date of Patent: Aug. 9, 1988

[54] DIFFUSER FOR VOLATILE LIQUID FLUIDS

[75] Inventors: Wendel Herbert; Wendel Serge, both of Sarreguemines, France

[73] Assignee: Societe International de Fabrication et de Diffusion de Produits Parfumes-I.P.P., Sarreguemines, France

[21] Appl. No.: 889,630

[22] Filed: Jul. 28, 1986

[30] Foreign Application Priority Data

Aug. 9, 1985 [FR] France ................. 85 12311
Oct. 25, 1985 [FR] France ................. 85 16013

[51] Int. Cl.⁴ .............................................. A61L 9/04
[52] U.S. Cl. ........................................ 239/6; 239/45
[58] Field of Search ............... 239/35, 34, 37, 42–44, 239/47, 51.5, 53, 57, 6; 222/187

[56] References Cited

U.S. PATENT DOCUMENTS

| | | | |
|---|---|---|---|
| 1,341,525 | 5/1920 | Vericel | 239/43 |
| 3,587,968 | 7/1969 | Hennart | 239/47 |
| 3,727,840 | 4/1973 | Nigro | 239/43 |
| 4,161,284 | 7/1979 | Rattan | 239/43 |
| 4,339,079 | 7/1982 | Sato et al. | 239/43 |
| 4,526,320 | 7/1985 | von Phillipp et al. | 239/515 X |

FOREIGN PATENT DOCUMENTS

| | | |
|---|---|---|
| 1231135 | 4/1960 | France . |
| 1316894 | 12/1962 | France . |
| 2486420 | 1/1982 | France . |
| 2486402 | 1/1982 | France . |
| 8500290 | 1/1985 | PCT Int'l Appl. . |

Primary Examiner—Andres Kashnikow
Assistant Examiner—Kevin P. Weldon
Attorney, Agent, or Firm—Sandler & Greenblum

[57] ABSTRACT

A diffuser for volatile liquids. The diffuser includes an absorbent carrier for accepting and diffusing a volatile liquid, a container for storing a volatile liquid, and a pointed element for piercing the perforable container to establish direct communication for flow of volatile liquid between the perforable container and the absorbent carrier.

21 Claims, 3 Drawing Sheets

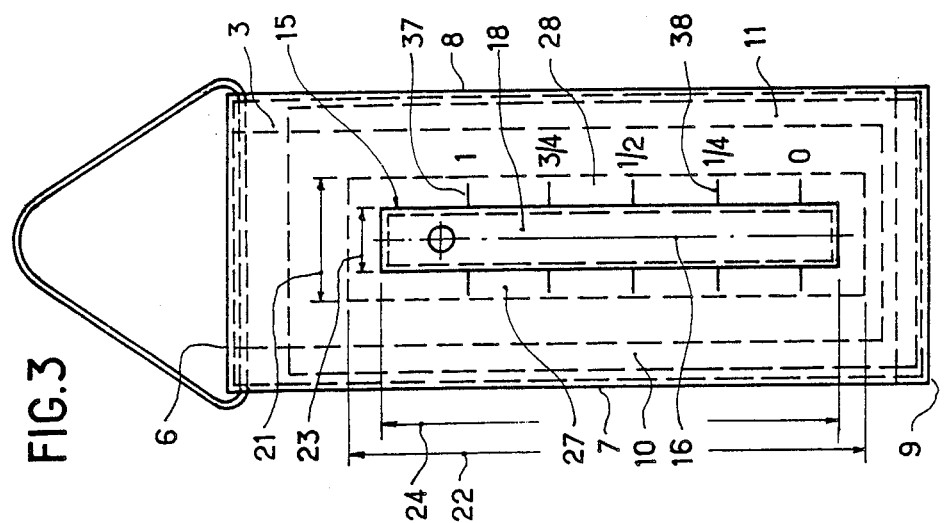
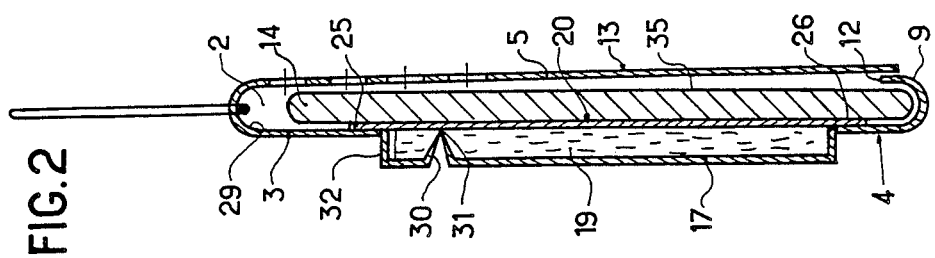
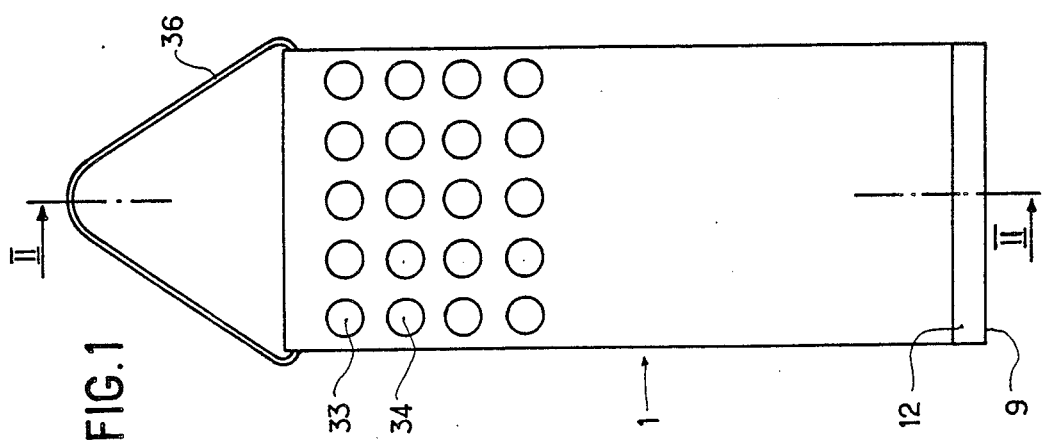

FIG. 4
FIG. 5
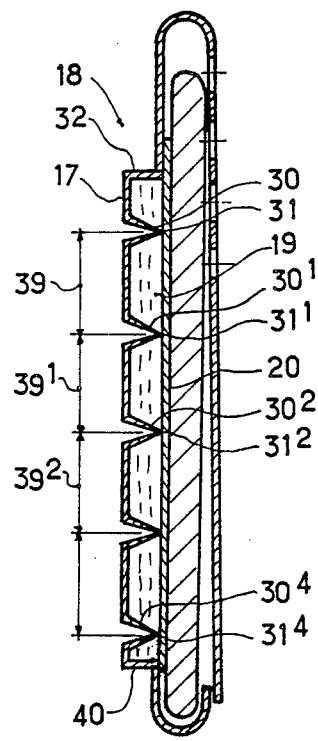
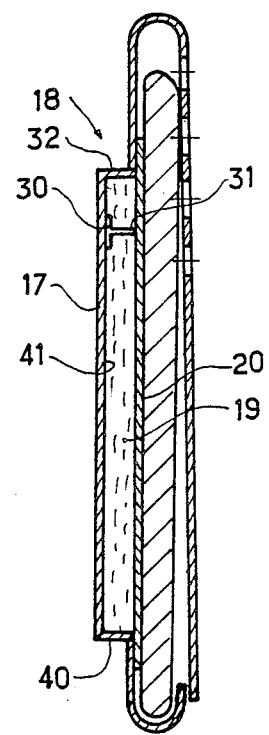

DIFFUSER FOR VOLATILE LIQUID FLUIDS

The invention concerns a diffuser for volatile liquid fluids such as deodorants, perfumes, essential oils, insecticides and others used in closed spaces such as cabins, vehicles, cupboards and similar, including a case provided with openings for letting pass the vapours emitted by the volatile liquid fluid, a small plate made of more or less porous or absorbent material lodged in the aforesaid case and a container sealed by a perforative membrane and filled with volatile liquid fluid.

In automobile vehicles or in public means of transport such as coaches, buses, underground and railway carriages, planes and others, the users are frequencty inconvenienced by malodourous emanations, evil smells, emanation of petrol fumes, of fuel fumes, etc . . . To remedy these inconveniences, diffusers have been devised that spread a pleasant odour in various closed spaces and, in particular, in automobile vehicles.

We already know diffusers with a small plate made of more or less porous or absorbent material lodged in a case. This case features an opening through which projects a bulb that contains perfume, the base of this bulb being in contact with the small plate. The aforesaid bulb has a hemispherical shape. The base of the bulb is pierced by means of a needle and the perfume soaks into the small plate. The perfume evaporates through holes made in the case. The aforesaid diffuser can be suspended and is fitted with a small chain for this purpose.

This diffuser, however, has several drawbacks. First, the user needs to have a needle for piercing the base of the hemispherical bulb. Furthermore and before piercing the base, he has to pierce the small plate. Therefore, part of the perfume may escape outside through the hole made in the small plate. The main drawback of this diffuser is, however, the leaking of the perfume. As a matter of fact, this diffuser is arranged in a vertical position. If the user, for any reason, pierces the base close to the bottom end of the case, all the perfume will leak out at once. The diffuser will thus run empty prematurely and the fragrance of the perfume may become too sharp and inconvenience the user.

The purpose of this invention is to remedy these drawbacks and to provide a diffuser where the user may proportion the liquid fluid flow as he likes.

With this purpose in mind, the invention concerns a diffuser of volatile liquid fluids such as deodorants, perfumes, essential oils, insecticides and others used, in particular, in closed spaces such as cabins, vehicles, cupboards and similar, including a case provided with openings for letting pass the vapours emitted by the volatile liquid fluid, a small carrier, or plate made of more or less porous or absorbent material lodged in the aforesaid case and a container sealed by a perforative membrane and filled with volatile liquid fluid, characterized in that the container is provided with a body fitted with means for piercing the perforative membrane and with means for withdrawing a specific dose of the volatile liquid fluid and for forcing the aforesaid dose under the effect of one pressure, at least, exercised by the user on the body, into the small plate made of more or less porous or absorbent material.

The advantages obtained through this invention consist essentially in that the volatile liquid fluid may have a certain viscosity as contrary to known diffusers where the soaking of the small plate made of more or less porous or absorbent material is achieved by simple leakage of the fluid enclosed in the container, the transfer of the volatile liquid fluid from the container to the aforesaid small plate is controlled by successive pressure movements applied to the container by the user. Furthermore, the withdrawal of deodorant, perfurme, essential oil, insecticide may be proportioned according to the user's wishes as well as according to the volume of the closed space in which the diffuser according to the invention is being used. In addition, this possibility of proportioning the amount withdrawn increases the length of time during which the aforesaid diffuser can be used.

The invention will be understood perfectly by referring to the description below given as an example with no restriction intended and to the appended drawing where:

FIG. 1 is a rear face elevation view of the diffuser according to the invention;

FIG. 2 is a sectional elevationview according to line II—II of FIG. 1;

FIG. 3 is a front face elevation view of the aforesaid diffuser;

FIG. 4 is a sectional elevation view according to line II—II of FIG. 1 of the diffuser made according to a different design:

FIG. 5 is a sectional elevation view according to line II—II of FIG. 1 of the diffuser made according to a different design:

Figure 6:
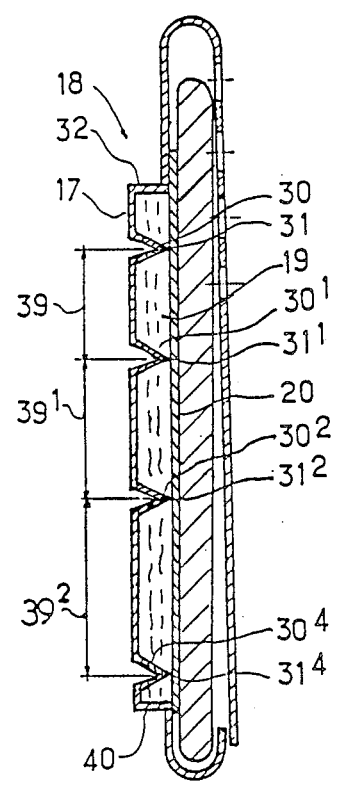
FIG. 6 is a sectional elevation view according to line II—II of FIG. 1 of the diffuser showing the pointed elements spaced at increasing intervals.

We refer to FIGS. 1 to 3.

The diffuser 1 includes a case 2 made of light-weight material such as cardboard, aluminium foil and similar. This case 2 is made of a body 3 that forms the front face 4 of the diffuser 1 and of a lid 5 that pivots around a top folding axis 6. On the longitudinal narrow sides 7, 8 and on the bottom narrow side 9 are made flanged edges 10, 11, 12 to which is fitted lid 5 by any means, with this lid 5 forming the rear face 13 of the diffuser 1.

A small plate 14 is installed in the space formed in this manner. This small plate is made of more or less porous or absorbent material. The small plate 14 practically takes up all the space available inside case 2.

In the body 3 is made an oblong opening 15 the longitudinal axis 16 of which is identical with the centre plane of the diffuser 1. Through this oblong opening 15 passes the body 17 of a container 18 that contains a volatile liquid fluid 19, with this body 17 projecting from the front face 4 of the case 2. Depending on the intended use of the diffuser 1, this volatile liquid fluid 19 is a deodorant, a perfume, an essential oil or even an insecticide. According to the invention, the container 18 has an elongated shape such as a parallelepiped or cylindrical shape of which the longitudinal axis is identical with the centre plane of the diffuser 1.

The container 18 is sealed by a membrane 20 of which the width 21 and the length 22 are greater than the width 23 and the length 24 of the oblong opening 15. Thus, the top edge 25 and the bottom edge 26 as well as the lateral edges 27,28 come to rest against the inside face 29 of the body 3. In this manner, the container 18 is kept in place and is unable to get outside the oblong opening 15 after the case 2 has been assembled. This membrane 20 rests on the small plate 14.

The body 17 of the container 18 is provided with a pointed element 30 of which the tip 31 is practically in contact with the membrane 20 and that projects from the inside face of the aforesaid body. This pointed element 30 is designed to pierce the membrane 20 when the diffuser 1 is being used. For this purpose, the membrane 20 has to be made of a thin impermeable and easily perforative foil such as an aluminium foil, plastic material foil, rubber foil and similar. Furthermore, the body 17 of the container 18 made to advantage of transparent or, at least, translucid material, has to be made of elastic material. The user, as a matter of fact, has to be able by applying pressure to the body 18 at the location of the pointed element 30, to drive the latter into the membrane 20 and by releasing the pressure, to have the pointed element 30 free the hole made in the membrane 20 to permit the volatile liquid fluid 19 to leak out and penetrate the small plate 14. This pointed element 30 is located close to the top edge 32 of the body 17 of the container 18. Thus, after the piercing, the amount of volatile liquid fluid 19 penetrating the small plate 14 is very small and the leaking ceases automatically when the level of the aforesaid liquid fluid contained in the body 17 has dropped slightly below the pointed element 30 as soon as the diffuser 1 has been suspended. According to a different design, the level of the volatile liquid fluid 19 is below the pointed element 30. Thus, even if pressure is applied accidentally to the body 17 and the membrane 20 is pierced as a result, no volatile liquid fluid 19 will penetrate the small plate 14. Only tilting the diffuser and applying pressure to the body 17 of the container 18 will ensure a proportioned outflow of the volatile liquid fluid 19.

To make the diffusing of the fragrance easier, the lid 5 is provided with a certain number of holes 33, 34 that pass through the lid 5 and issue at the rear face 35 of the small plate 14.

Prior to the assembling of the case 2, a suspension fixture 36 is fitted to allow for suspending the diffuser 1. This suspension fixture 36 is fitted on the side of the pointed element 30.

Possibly, the body 3 may be provided with markings 37,38 that allow for determining the amount of volatile liquid fluid 19 contained in the container 18.

It will thus be perfectly possible to proportion the amount of volatile fluid 19. As a matter of fact, having used the diffuser once i.e. when the level of the aforesaid liquid fluid 19 has dropped below the pointed element 30, the diffuser 1 has to be titled so that the pointed element 30 finds itself at the bottom. By applying pressure again to the body 17 of the container 18, a new amount of volatile liquid fluid 19 is withdrawn and the size of this amount depends on the number of pulses i.e. pressures applied to the aforesaid body 17.

Sometimes, however, it is desirable to have large-volume diffusers and to fit them permanently to a support such as a wall. It becomes thus impossible to tilt the diffuser without disassembling it, which inconveniences the user.

It is sometimes difficult, furthermore, to proportion the withdrawals of volatile liquid fluid as it is not possible to know the amount of liquid fluid withdrawn by each pulse. Therefore, the number of pulses applied to the body of the container may be too high which may result in a diffusion of vapours such that the user is inconvenienced.

We refer to FIG. 4.

The body of elongated shape 17 is provided with several pointed element 30, $30_1$, $30_2$ . . . These various pointed elements 30, $30_1$, $30_2$ . . . are arranged one underneath the other over the entire length of the body 17 of the container 18 and they are located preferably either according to a generatrix if the container 18 has a cylindrical form or according to the longitudinal axis if the container 18 has a body 17 of parallelepiped form.

Obviously, the distance 39 that separates two successive pointed elements 30, $30_1$ determines a specific dose determined in advance. Thus, after a first pressure has been applied to the body 17 at the place of the pointed element 30 for the outflow of a dose of volatile liquid fluid 19 through the hole made by the tip 31 into the membrane 20, the level of the aforesaid volatile liquid fluid contained in the body 17 will be slightly below the tip 31 of the pointed element 30.

By applying a second pressure to the body 17 at the place of the pointed element $30_1$, a second hole is made into the membrane 20, through which hole then leaks a new does of the volatile liquid fluid 19, with this outflow ceasing as soon as the level will be slightly below the tip $31_1$ of the pointed element $30_1$.

According to another design, the distances 39, $39_1$, $39_2$ . . . separating the various pointed elements 30, $30_1$, $30_2$ . . . are the same one as the other. Thus, each pressure applied successively to the pointed elements 30, $30_1$, $30_2$ . . . will cause an identical dose of volatile liquid fluid 19 to be withdrawn.

However, depending on the nature and on the degree of volatility, the air contained on top of the liquid fluid 19 may activate the latter's volatilization and the doses withdrawn should then become increasingly larger. In this manner and according to a different design, the distances 39, $39_1$, $39_2$ . . . will be increasingly larger from the top edge 32 down to the bottom edge 40 of the body 17 of the container 18.

For withdrawing all of the volatile liquid fluid 19 contained in the body 17, the bottom pointed element $30_4$ may be provided with a tip $31_4$ located close to the bottom edge 40 of the aforesaid body 17.

As shown by FIG. 4, the pointed element(s) 30, $30_1$, $30_2$ . . . are an integral part of the body 17 of the container 18. However, these pointed elements 30, $30_1$, $30_2$ . . . may consist of added elements kept in place at the inside face 41 of the body 17 of the container 18 by any means of attachment (cfr. FIG. 5).

We claim:

1. A diffuser for volatile liquids comprising:
    (a) an absorbent carrier for accepting and diffusing a volatile liquid;
    (b) a perforable container for storing a volatile liquid; and
    (c) piercing means, situated on the interior of said perforable container, for piercing said perforable container to establish direct communication for discharge of volatile liquid from said perforable container to said absorbent carrier, said piercing means being positioned for controlling the amount of volatile liquid that discharges from said perforable container in response to the piercing of said perforable container.

2. The diffuser as defined by claim 1 wherein said perforable container is sealed by perforable membrane adjacent said absorbent carrier, and said piercing means comprises means for piercing said perforable membrane.

3. The diffuser as defined by claim 1 wherein said perforable container comprises a first end and a second end, and said piercing means comprises a plurality of piercing means spaced at regular intervals between said two ends.

4. The diffuser as defined by claim 1 wherein said piercing means is integral with said container.

5. The diffuser as defined by claim 1 wherein said piercing means comprises one piercing means.

6. The diffuser as defined by claim 1 wherein said container comprises a paralleliped body.

7. The diffuser as defined by claim 1 wherein said container comprises a cylindrical body.

8. The diffuser as defined by claim 1 wherein said perforable container contains an amount of volatile liquid.

9. The diffuser as defined by claim 5 wherein said perforable container comprises an upper end and a lower end, and said one piercing means is situated between said upper end and said lower end, whereby said one piercing means comprises means for discharging volatile liquid situated above said piercing means.

10. The diffuser as defined by claim 9 wherein said diffuser is adapted for tilting to raise liquid above said one piercing means.

11. The diffuser as defined by claim 9 wherein:
(a) said container contains an amount of volatile liquid having an upper level situated below the upper end of said container; and
(b) said one piercing means comprises means for piercing said container below the level of said volatile liquid.

12. The diffuser as defined by claim 9 wherein:
(a) said container contains an amount of volatile liquid having an upper level situated below the upper end of said container; and
(b) said one piercing means comprises means for piercing said container above the level of said volatile liquid.

13. The diffuser as defined by claim 1 wherein said perforable container comprises an upper end and a lower end, and said piercing means comprises a plurality of piercing means spaced at intervals from said upper end to said lower end, the lowest of said plurality of piercing means being located close to the lower end of said container.

14. The diffuser as defined by claim 1 wherein said perforable container comprises an upper end and a lower end, and wherein said piercing means comprises a plurality of piercing means spaced at regular intervals from said upper end to said lower end.

15. The diffuser as defined by claim 1 wherein said perforable container comprises an upper end and a lower end, and wherein said piercing means comprises a plurality of piercing means spaced at increasing intervals from said upper end to said lower end.

16. The diffuser as defined by claim 1 wherein said perforable container comprises an oblong, elastic, transparent, body having a plane of symmetry, mounted on a support having a plane of symmetry, said planes of symmetry being coincident.

17. A method for controlling the amount of volatile liquid discharged, from a perforable container, for storing a volatile liquid, having an upper and a lower end, to an absorbent carrier for accepting and defusing said volatile liquid, comprising:
(a) successively perforating said perforable container at points between said upper end and said lower end of said perforable container, with a plurality of piercing means that are in fluid contact with said volatile liquid prior to perforation of said perforable container; and
(b) discharging the volatile liquid, situated above said each successive point of perforation, from said perforable container to said absorbent carrier.

18. The method as defined by claim 17 wherein said volatile liquid is communicated directly from said perforable container to said absorbent carrier.

19. A method for controlling the amount of volatile liquid discharged, from a perforable container, for storing a volatile liquid, having an upper and lower end, to an absorbent carrier for accepting and defusing said volatile liquid, comprising:
(a) perforating said perforable container at a point between said upper end and said lower end of said perforable container, with a piercing means that is in fluid contact with said volatile liquid prior to perforation of said perforable container; and
(b) discharging the volatile liquid, situated above said point of perforation, from said perforable container to said absorbent carrier; and
(c) tilting said container to raise volatile fluid above said point of perforation; and
(d) discharging volatile liquid raised above said point of perforation from said perforable container to said absorbent carrier.

20. A method for discharging predetermined amounts of volatile liquid, from a perforable container having an upper end and a lower end, to an absorbent carrier for absorbing and diffusing said volatile liquid, comprising:
(a) perforating said perforable container at successive points between said upper end and said lower end of said perforable container; and
(b) after perforating said container at a point of perforation, discharging volatile liquid situated above said point of perforation.

21. A diffuser for volatile liquids comprising:
(a) an absorbent carrier for accepting and diffusing a volatile liquid;
(b) a perforable container for storing a volatile liquid, said perforable container comprising a first end and a second end;
(c) piercing means, situated on the interior of said perforable container, for piercing said perforable container to establish direct communication for discharge of volatile liquid from said perforable container to said absorbent carrier, said piercing means comprising a plurality of piercing means spaced at increasing intervals from one of said ends to the other.

* * * * *